US009565995B2

(12) United States Patent
Nguyen et al.

(10) Patent No.: US 9,565,995 B2
(45) Date of Patent: Feb. 14, 2017

(54) ENDOSCOPE CHANNEL SEPARATOR

(75) Inventors: Nick N. Nguyen, Silverado, CA (US);
Walter Francovich, Pierrefonds (CA);
Philippe Conseil, Roxboro (CA)

(73) Assignee: ETHICON, INC., Somerville, NJ (US)

( * ) Notice: Subject to any disclaimer, the term of this patent is extended or adjusted under 35 U.S.C. 154(b) by 1079 days.

(21) Appl. No.: 12/998,460

(22) PCT Filed: Oct. 5, 2009

(86) PCT No.: PCT/US2009/059517
§ 371 (c)(1),
(2), (4) Date: Aug. 29, 2011

(87) PCT Pub. No.: WO2010/045051
PCT Pub. Date: Apr. 22, 2010

(65) Prior Publication Data
US 2011/0298169 A1    Dec. 8, 2011

Related U.S. Application Data

(60) Provisional application No. 61/196,714, filed on Oct. 13, 2008.

(51) Int. Cl.
*B25B 1/00* (2006.01)
*A61B 1/12* (2006.01)
*A61B 1/00* (2006.01)

(52) U.S. Cl.
CPC ........... *A61B 1/125* (2013.01); *A61B 1/00057* (2013.01); *A61B 1/00137* (2013.01); *A61B 1/00068* (2013.01)

(58) Field of Classification Search
CPC ....... A61B 1/12; A61B 1/125; A61B 1/00137; A61B 1/00057
(Continued)

(56) References Cited

U.S. PATENT DOCUMENTS 1,492,521 A    4/1924    Meyer
2,996,317 A    8/1961    Kibbie et al.
(Continued)

FOREIGN PATENT DOCUMENTS

CN    1872349 A    12/2006
EP    1055860 A2    11/2000
(Continued)

OTHER PUBLICATIONS

International Search Report for International Application No. PCT/US2009/059517 mailed Dec. 23, 2009, 3 pages.
(Continued)

*Primary Examiner* — Joseph J Hail
*Assistant Examiner* — Brian Keller
(74) *Attorney, Agent, or Firm* — K&L Gates LLP

(57) ABSTRACT

A decontamination system including a test fixture configured to engage an endoscope in order to retain the test fixture thereto, wherein the endoscope can comprise a valve chamber and a valve removable from the valve chamber such that the test fixture can be inserted therein. The test fixture can comprise, first, a frame having a first gripping portion and a valve member analog extending from the frame, and, second, a housing having a second gripping portion movable relative to the frame between a locked position and an unlocked position, wherein the second gripping portion is configured to be moved toward the first gripping portion to position the housing in its unlocked position. The second gripping portion can be configured to be moved away from the first gripping portion to position the housing in its locked position such that the housing can engage a locking feature on the endoscope.

20 Claims, 14 Drawing Sheets

(58) Field of Classification Search
USPC .................. 269/86; 29/407.01, 464, 559
See application file for complete search history.

(56) References Cited

U.S. PATENT DOCUMENTS

| | | | |
|---|---|---|---|
| 3,682,503 A | 8/1972 | Bloom | |
| 3,719,375 A | 3/1973 | Nordin | |
| 3,899,200 A | 8/1975 | Gamble | |
| 4,116,476 A | 9/1978 | Porter et al. | |
| 4,483,510 A | 11/1984 | Palau et al. | |
| 4,637,378 A * | 1/1987 | Sasa | 600/155 |
| 4,753,268 A * | 6/1988 | Palau | 137/595 |
| 4,981,469 A | 1/1991 | Whitehouse et al. | |
| 5,167,220 A | 12/1992 | Brown | |
| 5,234,417 A | 8/1993 | Parks et al. | |
| 5,534,228 A | 7/1996 | Wesseler | |
| 5,749,829 A * | 5/1998 | Yokoi et al. | 600/153 |
| 5,806,832 A | 9/1998 | Larbuisson | |
| 5,911,443 A | 6/1999 | LeQuere | |
| 6,095,971 A | 8/2000 | Takahashi | |
| 6,158,829 A * | 12/2000 | Nielsen | 312/208.1 |
| 6,273,478 B1 | 8/2001 | Benett et al. | |
| 6,454,314 B1 | 9/2002 | Grosspietsch et al. | |
| 6,485,684 B1 | 11/2002 | Mapson et al. | |
| 6,840,548 B2 | 1/2005 | Lacroix | |
| 6,958,017 B1 * | 10/2005 | Toombs, Jr. | 472/118 |
| 6,986,736 B2 * | 1/2006 | Williams et al. | 600/101 |
| 7,152,621 B1 * | 12/2006 | Huetinck | F16K 5/0414 137/385 |
| 7,153,296 B2 | 12/2006 | Mitchell | |
| 7,316,425 B2 | 1/2008 | Poder | |
| 7,561,473 B2 | 7/2009 | Mokhlesi et al. | |
| 7,604,262 B2 | 10/2009 | Elfein et al. | |
| 7,686,761 B2 | 3/2010 | Jackson et al. | |
| 7,753,415 B2 | 7/2010 | Tiberghien et al. | |
| 7,828,336 B2 | 11/2010 | Gammons | |
| 7,837,646 B2 | 11/2010 | Eidinger et al. | |
| 7,887,102 B2 | 2/2011 | Tiberghien et al. | |
| 7,901,350 B2 * | 3/2011 | Yamazaki | 600/159 |
| 8,113,548 B2 | 2/2012 | Gunderson | |
| 2006/0135851 A1 * | 6/2006 | Yamazaki | 600/159 |
| 2009/0049671 A1 * | 2/2009 | O'Hara | F16K 1/48 29/213.1 |
| 2011/0298209 A1 | 12/2011 | Nguyen et al. | |
| 2012/0007352 A1 | 1/2012 | Nguyen et al. | |

FOREIGN PATENT DOCUMENTS

| | | |
|---|---|---|
| EP | 1433410 A1 | 6/2004 |
| EP | 1728466 A2 | 12/2006 |
| EP | 1762172 A2 | 3/2007 |
| GB | 2226861 A | 7/1990 |
| JP | 2-209690 A | 8/1990 |
| JP | 2-225898 A | 9/1990 |
| JP | 5-49596 A | 3/1993 |
| JP | 7-67938 A | 3/1995 |
| JP | 2000-70218 A | 7/2000 |
| JP | 2002-71073 A | 3/2002 |
| JP | 2004-202247 A | 7/2004 |
| JP | 2005-58258 A | 3/2005 |
| JP | 2006-55325 A | 3/2006 |
| JP | 2006-149556 A | 6/2006 |
| JP | 2007-289723 A | 11/2007 |
| WO | WO 2006/062912 A1 | 6/2006 |

OTHER PUBLICATIONS

International Preliminary Report on Patentability for International Application No. PCT/US2009/059517 issued Apr. 19, 2011, 6 pages.

* cited by examiner

ENDOSCOPE CHANNEL SEPARATOR

CROSS-REFERENCE TO RELATED APPLICATIONS

This application is a National Stage entry of International Application No. PCT/US2009/059517, entitled ENDOSCOPE CHANNEL SEPARATOR, filed on Oct. 5, 2009, which claims the benefit of U.S. Provisional Patent Application No. 61/196,714, entitled ENDOSCOPE CHANNEL SEPARATOR, filed on Oct. 13, 2008.

BACKGROUND

Field of the Invention

The present invention generally relates to the reprocessing, or decontamination, of medical instruments.

Description of the Related Art

In various circumstances, an endoscope can include an elongate portion, or tube, having a distal end which can be configured to be inserted into the body of a patient and, in addition, a plurality of channels extending through the elongate portion which can be configured to direct water, air, and/or any other suitable fluid into a surgical site. In some circumstances, one or more channels in an endoscope can be configured to guide a surgical instrument into the surgical site. In any event, an endoscope can further include a proximal end having inlets in fluid communication with the channels and, in addition, a control head section having one or more valves, and/or switches, configured to control the flow of fluid through the channels. In at least one circumstance, an endoscope can include an air channel, a water channel, and one or more valves within the control head configured to control the flow of air and water through the channels.

Decontamination systems can be used to reprocess previously-used medical devices, such as endoscopes, for example, such that the devices can be used once again. During the decontamination process of an endoscope, the air and water channels within the endoscope can be evaluated in order to verify that the channels are unobstructed. In certain decontamination systems, a source of fluid can be attached to, or otherwise operably associated with, the channel inlets of the endoscope such that fluid from the fluid source, such as water, for example, can flow through the channels. In such systems, the rate in which the fluid flows through a channel can be measured to determine whether the flow of fluid through the channel is obstructed. For example, if the actual flow rate of the fluid through a channel is slower than expected, it is possible that the channel is at least partially obstructed and the system can convey to the operator that additional decontamination of the endoscope, or at least further investigation, may be warranted.

The foregoing discussion is intended only to illustrate some of the shortcomings present in the field of the invention at the time, and should not be taken as a disavowal of claim scope.

SUMMARY

In at least one form of the invention, a test fixture, or endoscope channel separator, can be configured to engage at least a portion of an endoscope in order to retain the test fixture to the endoscope. In various embodiments, an endoscope can include a control head having a valve and a valve chamber, wherein the valve can be removed from the valve chamber such that the test fixture can be inserted therein. In at least one embodiment, the test fixture can include a valve member analogue configured to be inserted into the valve chamber, wherein, in some embodiments, the valve member analogue can comprise a disposable valve member analogue removably attached to the test fixture. In certain embodiments, the test fixture can comprise a frame having a first gripping portion and a housing having a second gripping portion, wherein the housing can be movable between a locked position and an unlocked position relative to the frame, and wherein the second gripping portion can be configured to be moved toward the first gripping portion to position the housing in its unlocked position. In certain embodiments, the second gripping portion can be configured to be moved away from the first gripping portion to position the housing in its locked position such that a locking feature on the housing can engage a locking feature on the endoscope. In at least one embodiment, the test fixture can further comprise a spring positioned intermediate the housing and the frame, wherein the spring can be configured to bias the housing into its locked position. In various embodiments, the test fixture can further comprise a lifting member movable relative to the frame, wherein the lifting member can be movable between a first position and an extended position, and wherein the lifting member can be configured to engage the endoscope when it is in its extended position to move the frame relative to the endoscope.

This Summary is intended be briefly outline certain embodiments of the subject application. It should be understood that the subject application is not limited to the embodiments disclosed in this Summary, and is intended to cover modifications that are within its spirit and scope, as defined by the claims. It should be further understood that this Summary should not be read or construed in a manner that will act to narrow the scope of the claims.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Figure 10:
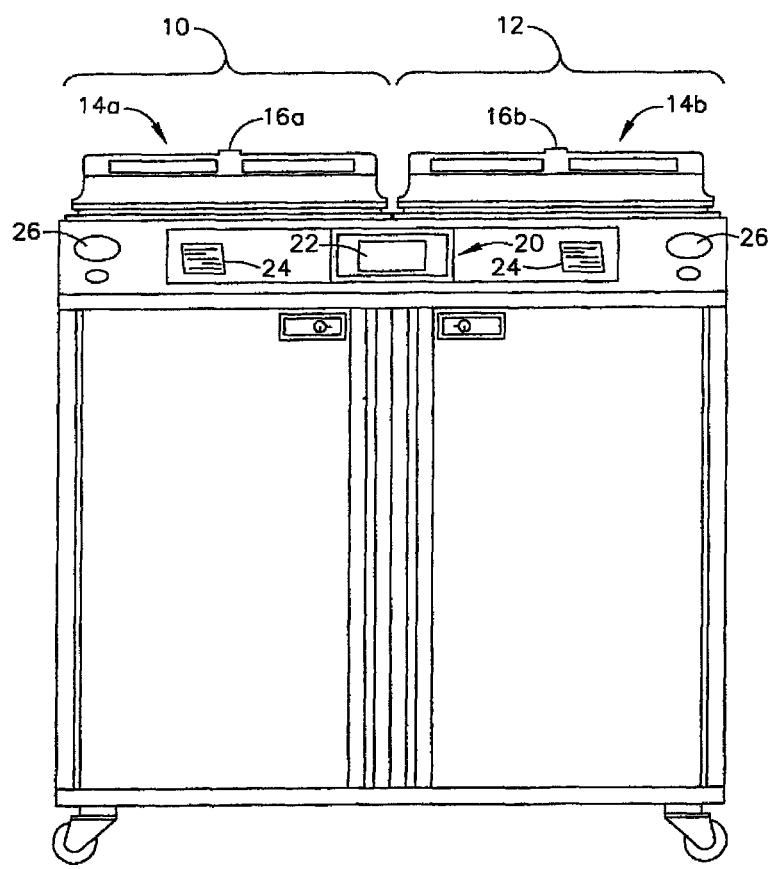
FIG. 10 is a front elevational view of a decontamination apparatus.

One embodiment of a decontamination apparatus is depicted in FIG. 10 which may be configured for decontaminating endoscopes and/or other medical devices. A variety of different systems and devices for decontaminating and reprocessing medical devices such as, for example, endoscopes are known in the art. Accordingly, the scope of protection afforded to the various arrangements of the present invention should not be limited to a particular processor or decontamination apparatus configuration.

In various arrangements, the decontamination apparatus can generally include one or more stations for decontaminating a medical device. In at least one embodiment, the decontamination apparatus can include a first station 10 and a second station 12 which can be at least substantially similar in all respects to provide for the decontamination of a medical device in series or two different medical devices simultaneously. In at least one embodiment, first and second decontamination basins, or chambers, 14a, 14b can receive the contaminated devices, wherein each chamber 14a, 14b can be selectively sealed by a lid 16a, 16b, respectively, preferably in a microbe-blocking relationship to prevent the entrance of microbes into the chambers 14a, 14b during the operation of the decontamination apparatus. In various embodiments, the lids can include a microbe removal or HEPA air filter, for example, for providing a flow of vented air therethrough.

A control system 20 can include one or more microcontrollers, such as a programmable logic controller (PLC), for example, for controlling the operation of the decontamination apparatus. Although one control system 20 is shown herein as controlling both decontamination stations 10, 12, each station 10, 12 can include a dedicated control system. In various embodiments, the decontamination apparatus can further include at least one visual display 22 configured to display decontamination parameters and machine conditions to an operator and, in addition, at least one printer 24 configured to print a hard copy output of the decontamination parameters which can be filed in a record-keeping system and/or attached to the decontaminated device or its storage packaging. In at least one embodiment, the visual display 22 can be combined with a touch screen input device to facilitate the use of control system 20. In various embodiments, a keypad or the like can be provided for the input of decontamination process parameters and otherwise controlling the decontamination apparatus. Gauges, such as gauges 26, for example, can include pressure meters and/or any other suitable measuring device which can provide digital and/or analog output of decontamination or medical device leak testing data. Various leak testing devices and methods are disclosed in U.S. Pat. No. 6,986,736, entitled AUTOMATED ENDOSCOPE REPROCESSOR CONNECTION INTEGRITY TESTING, which issued on Jan. 17, 2006, the entire disclosure of which is hereby incorporated by reference herein. Other devices and methods are disclosed in concurrently-filed, co-pending U.S. patent applications entitled FLUID CONNECTOR FOR ENDOSCOPE REPROCESSING SYSTEM, Ser. No. 13/089,109, and QUICK DISCONNECT FLUID CONNECTOR, Ser. No. 13/089,107, the entire disclosures of which are incorporated by reference herein.

Figure 11:
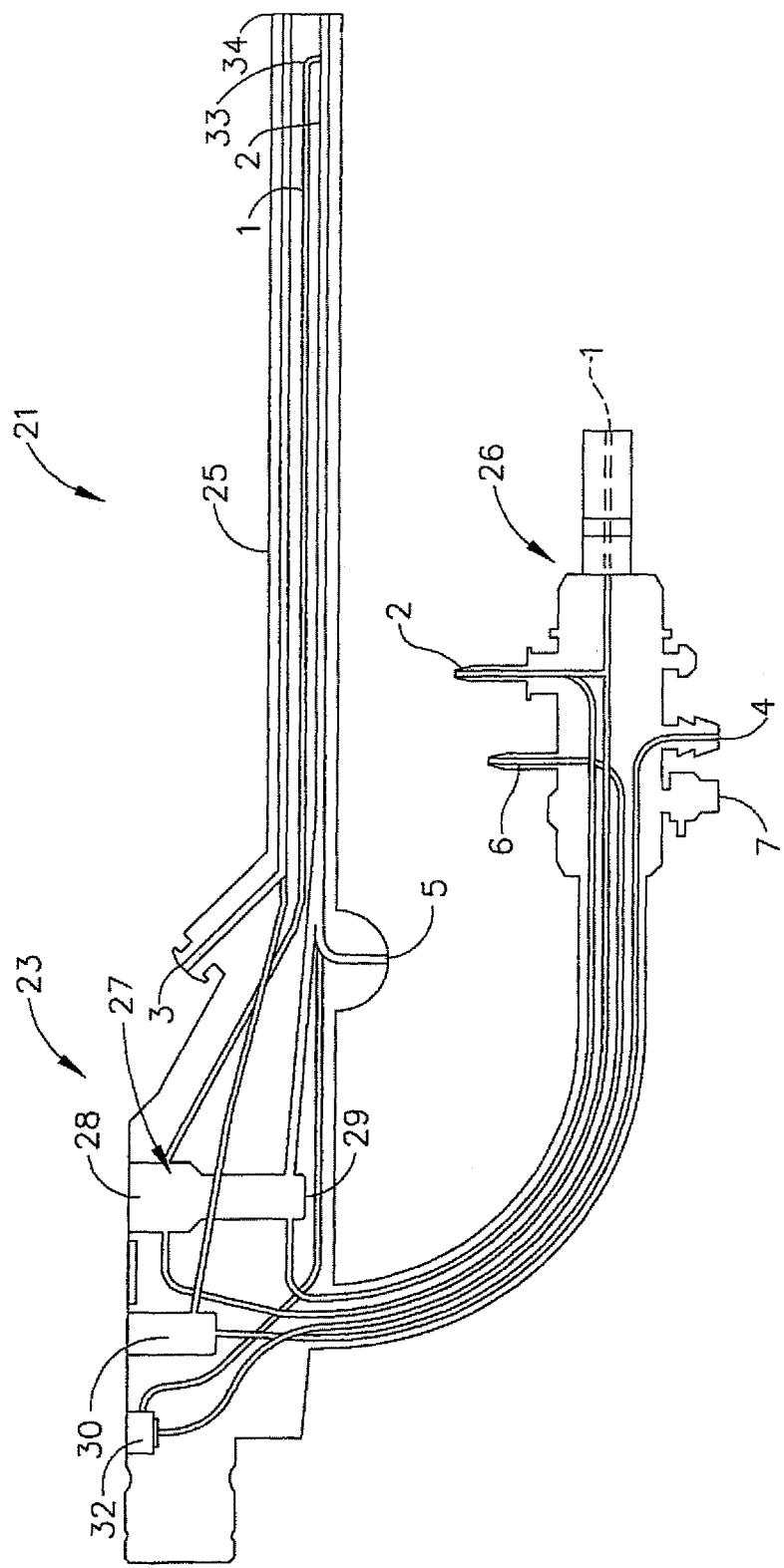
FIG. 11 is a schematic representation of an endoscope.

In various embodiments, referring to FIG. 11, an endoscope, such as endoscope 21, for example, can include elongate portion, or insertion tube, 25 which can be configured to be inserted into the body of a patient through a trocar, for example. In at least one embodiment, endoscope 21 can further include proximal portion, or light guide section, 26, control head section 23, and one or more channels, or lines, for conveying a fluid. More particularly, an endoscope can include one or more channels extending therethrough which can be configured to convey a fluid, such as water, air, and/or carbon dioxide, for example, into a surgical site. As used herein, the term "fluid" may comprise liquid materials such as water, decontamination and sterilization liquids, etc., as well as materials in a vapor or gaseous state, such as, for example, air, carbon dioxide and various other gases. As used herein, the term "in fluid communication" means that a fluid-carrying or fluid-transporting member (e.g., pipe, hose, conduit, channel, etc.) is coupled to another fluid-carrying or fluid-transporting member so as to permit the fluid to flow or otherwise migrate from one member to the other.

Figure 14:
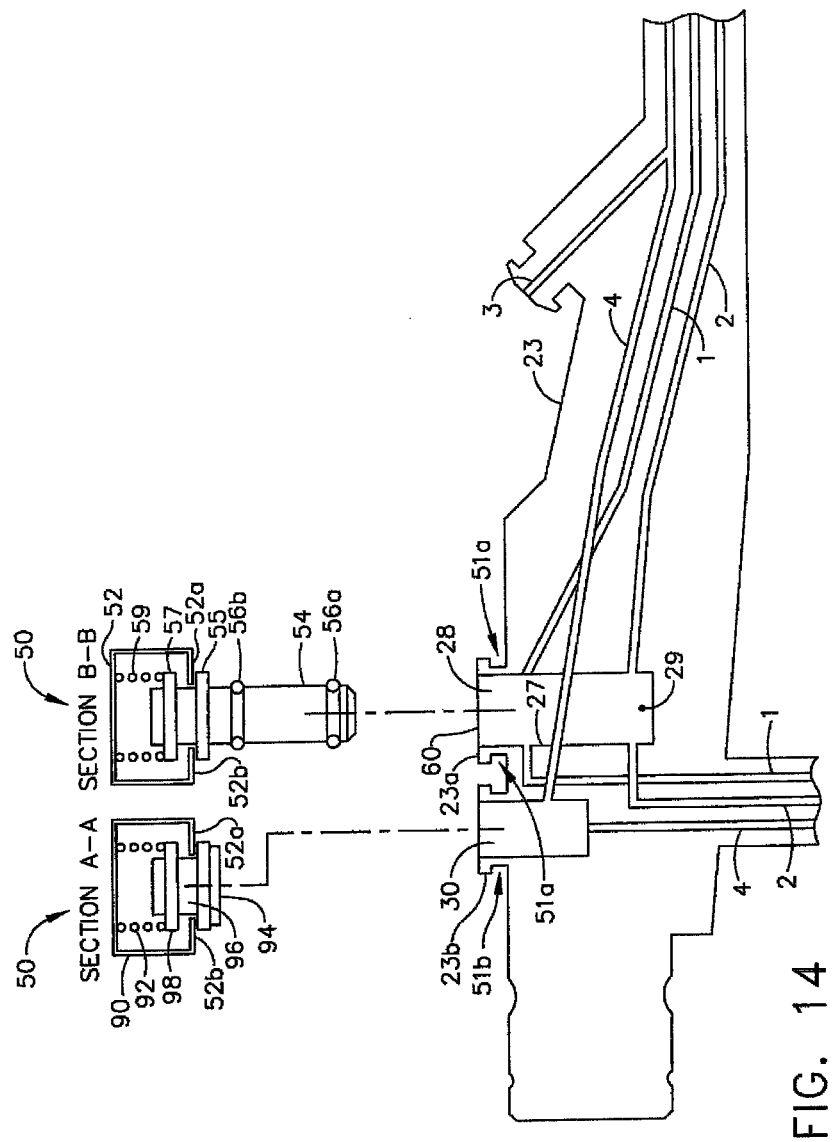
FIG. 14 is a partial cross-sectional view of the channel separator of FIG. 13 and the endoscope of FIG. 11.

Referring to FIGS. 11 and 14, endoscope 21 can include a first channel 1 which can extend from an inlet at proximal end 26, for example, through at least a portion of control head section 23 and elongate portion 25, and to an outlet at distal end 34. In various embodiments, channel 1 can be configured to convey air to the surgical site, for example. Endoscope 21 can also include second channel 2 which can be configured to convey water from an inlet at proximal end 26, for example, through at least a portion of control head section 23 and elongate portion 25, and to an outlet at distal end 34.

In various embodiments, again referring to FIGS. 11 and 14, an endoscope can further include additional channels, such as channel 4, for example, which can be configured to provide a vacuum, or suction, to a surgical site. An endoscope can also include channel 6 for providing carbon dioxide. In at least one embodiment, an endoscope can further include biopsy channel 3, for example, which can be configured to receive a surgical instrument therein such that the surgical instrument can be guided into the surgical site through the endoscope. In some embodiments, an endoscope can further include a channel, such as channel 5, for example, which can be configured to convey a highly-pressurized jet of water that is discharged from distal end 34. In at least one embodiment, proximal end 26 can further include leak test connector 7 which can be configured to introduce a pressurized fluid and/or vacuum into the endoscope in order to inspect for leaks between the channels, for example.

In various embodiments, referring to FIG. 11, control head section 23 can include valve chamber 32 which can be configured to receive a valve element therein such that the valve element can control the flow of carbon dioxide, for example, through the endoscope. In at least one embodiment, the valve element can comprise a stopcock, for example, which can be configured to allow carbon dioxide to flow through channel 6 when the stopcock is in a first, or open, position and prevent, or at least substantially prevent, the flow of carbon dioxide through channel 6 to distal end 34 when the stopcock is rotated into a second, or closed, position. Similarly, in various embodiments, control head section 23 can include valve chamber 30 which can be configured to receive a valve element therein which can be configured to control whether vacuum, or suction, can be communicated to distal end 34 through channel 4. In various embodiments, as discussed in greater detail further below, control head section 23 can include a valve chamber, such as valve chamber 27, for example, comprising a first portion 28 in fluid communication with channel 1 and, in addition, a second portion 29 in fluid communication with channel 2. For the purposes of this application, any number of valves, channels, and/or any other suitable devices can be deemed to be in fluid communication with each other if a fluid can flow between the devices whether by pressure differential, gravity feed, and/or any other suitable manner.

In various embodiments, further to the above, valve chamber 27 can be configured to receive a valve element having a seal configured to sealingly separate valve chamber 27 into portions 28 and 29. In at least one embodiment, the seal can be configured such that air flowing through channel 1 does not flow into, or at least substantially flow into, second portion 29, for example. Similarly, the seal can also be configured such that water flowing through channel 2 does not flow into, or at least substantially flow into, first portion 28. In various embodiments, although not illustrated, such a valve element can assist in sealingly separating two or more channels such that fluids flowing therethrough can be discharged from separate orifices in the distal end of an endoscope. In at least one alternative embodiment, referring to FIG. 11, channels 1 and 2 can be placed in fluid communication with one another at a location, such as location 33, for example, which is downstream from valve chamber 27 such that the air and water flowing through channels 1 and 2, respectively, can be discharged from the endoscope through a common orifice.

Figure 12:
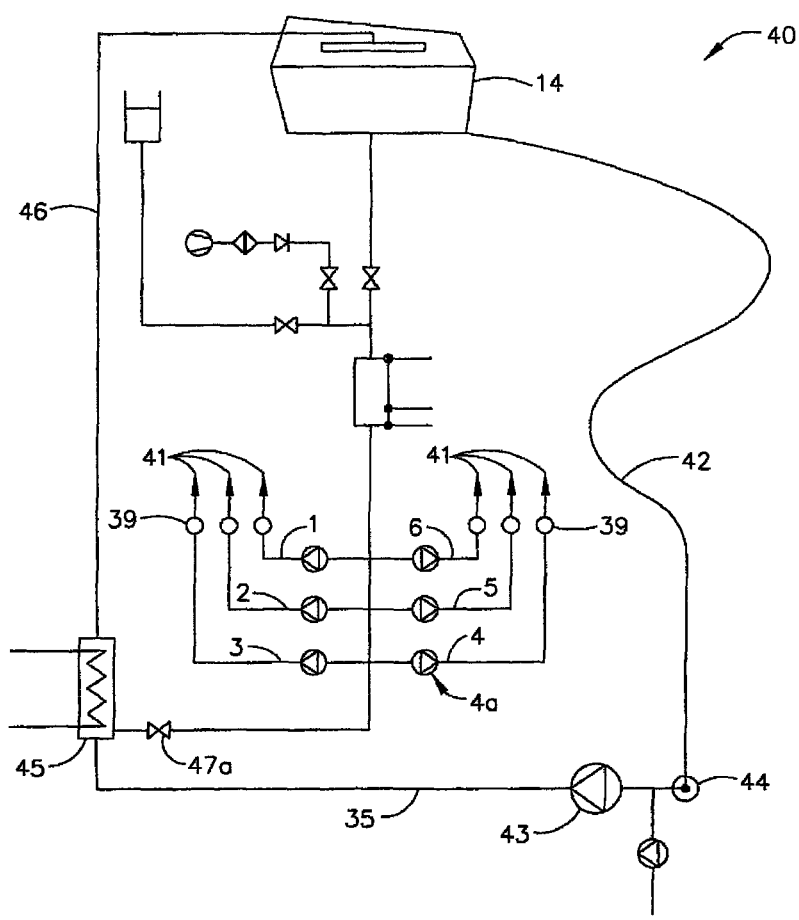
FIG. 12 is a schematic representation of a decontamination system.

After an endoscope has been used, it can be reprocessed such that it can be used once again. In various circumstances, a decontamination apparatus, such as those described above, for example, can be utilized to decontaminate the endoscope and/or evaluate whether the endoscope has been properly decontaminated. In at least one circumstance, water, sterilant, and/or any other suitable fluid, can be flushed through one or more of the channels of the endoscope to remove debris, and/or any other foreign matter, which may have entered into the channels. In various embodiments, referring to FIG. 12, decontamination system 40 can include basin 14 which can be configured to receive at least a portion of an endoscope therein and, in addition, tube 42 which can, in at least one embodiment, be configured to receive at least a portion of, or be in fluid communication with, elongate portion 25 of the endoscope. In at least one embodiment, decontamination system 40 can further include circulation pump 43 which can be configured to circulate fluid from basin 14, for example, through endoscope 21 and/or tube 42, and into line 35. In certain embodiments, pump 43 can also be configured to push the fluid through heater 45 and into line 46 such that the fluid can be circulated back into basin 14, for example. In various embodiments, decontamination system 40 can further include valve 47a which can be configured to divert at least a portion of the fluid flowing within line 35 through the channels of the endoscope. More particularly, in at least one embodiment, decontamination system 40 can include six fluid connectors 41 which can be configured to receive fluid from line 35, wherein each of the six connectors 41 can be placed in fluid communication with one of the six channels of the endoscope, i.e., channels 1-6, for example, such that fluid can flow therethrough.

Before, during, and/or after the endoscope has been subjected to a decontamination process, for example, the channels of the endoscope can be evaluated to determine whether debris, or any other foreign substance, remains in the channels. In various embodiments, referring to FIG. 12, a channel pump 4a associated with channel 4, for example, can be activated to motivate fluid through channel 4. In at least one such embodiment, a sensor, such as sensor 39, for example, can be configured to measure the flow rate of the fluid flowing through channel 4, wherein the flow rate measured by the sensor can be compared to an expected, or predicted, flow rate which represents the flow rate of the fluid when the channel is unobstructed. In various embodiments, the predicted flow rate through channel 4, for example, can be calculated in view of the parameters of channel pump 4a, the diameter, length, and/or various other properties of channel 4, and/or other features of the decontamination system. The predicted flow rate can also be empirically determined. In either event, in the event that the measured flow rate matches, or at least substantially matches, the expected flow rate, or is within a range of flow rates, for a given channel, the decontamination apparatus can convey to the operator that the existence of debris or a foreign substance within the channel is unlikely. In certain embodiments, sensors 39 can include pressure sensors which can be configured to detect the pressure of the fluid flowing through one or more channels. In the event that such a sensor 39 detects a fluid pressure that is above and/or below an expected pressure, or range or pressures, the decontamination apparatus can communicate to the operator that a foreign substance is present or that the endoscope, for example, is defective in some manner. In at least one such embodiment, the pressure sensors can, as a result, indirectly measure the rate of the fluid flowing through the channels.

In various embodiments, further to the above, the measured flow rate and/or pressure of a fluid flowing through an endoscope channel does not have to exactly match the expected flow rate and/or pressure. In at least one embodiment, a channel can be deemed unobstructed if the measured flow rate is within an acceptable range relative to the expected flow rate, for example. In the event that the measured flow rate is not within the acceptable range, the decontamination apparatus can convey to the operator that the channel may be obstructed and that further investigation may be warranted. By way of example, if debris, or other foreign matter, is present within the channel, the debris may retard or reduce the flow rate of the fluid through the channel and the decontamination apparatus. Correspondingly, the debris or foreign matter may cause the pressure of the fluid to increase. In order to assist the operator in diagnosing the problem, the control system of the decontamination apparatus can convey information to the operator including which channel is being tested, the measured flow rate and/or pressure, and/or the percentage by which the measured value is different than the predicted value. In certain embodiments, a sensor can be configured to generate a series of signal pulses which correspond to the amount, or rate, of fluid flowing through a channel. For example, a sensor can generate signal pulses at a slower rate when the flow of fluid through or by the sensor is slower and, correspondingly, the sensor can generate signal pulses at a higher rate when the flow of fluid through or by the sensor is faster. In some circumstances, the rate in which the sensor produces signal pulses can be directly proportional to the rate in which the fluid is flowing through the channel. In at least one such embodiment, the decontamination apparatus can be configured to receive such signal pulses and, in view of such information, determine whether the fluid flow is appropriate.

Figure 13:
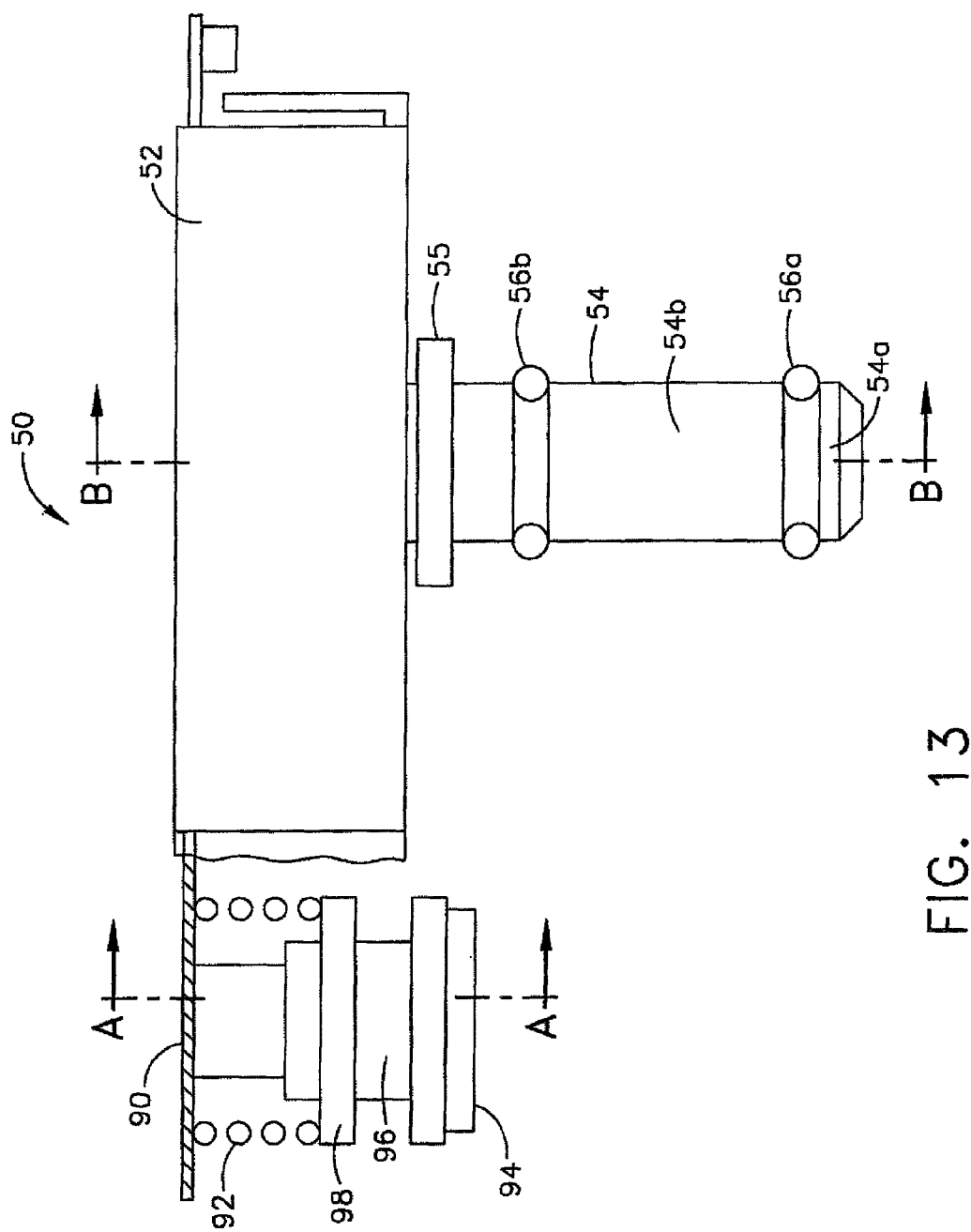
FIG. 13 is an elevational view of a test fixture, or channel separator, for use with an endoscope.

In various circumstances, further to the above, the valve elements within an endoscope can be removed from their respective valve chambers such that the valve elements can be decontaminated separately, for example. In the event that the valve elements are removed from the valve chambers, one or more test fixtures, or channel separators, can be operably engaged with the endoscope in order to prevent the test fluids flowing through the channels of the endoscope from escaping from the endoscope through an open end of the valve chambers. In at least one embodiment, referring to FIGS. 13 and 14, channel separator 50 can include a connector portion 90, a biaser, such as a spring 92, for example, and a face seal 94, wherein spring 92 can be configured to bias face seal 94 against a sealing surface within and/or surrounding valve chamber 30, for example. In at least one such embodiment, spring 92 can apply a sufficient biasing force to face seal 94 in order to prevent, or at least substantially prevent, fluid from escaping from valve chamber 30. In at least the illustrated embodiment, face seal 94 can be mounted to valve element analogue 96, wherein valve element analogue 96 can include a projection, such as substantially annular projection 98, for example, which can be configured to receive the biasing force from spring 92 and transmit the biasing force to face seal 94. In certain embodiments, a radial seal can be utilized to seal a valve element analogue within a valve chamber.

Further to the above, referring again to FIGS. 13 and 14, channel separator 50 can further include valve element analogue 54 which can be configured to be positioned within and sealingly separate valve chamber 27 into first portion 28 and second portion 29. In various embodiments, channel separator 50 can further include seal 56a positioned around at least a portion of valve element analogue 54 wherein seal 56a can be configured to sealingly engage the sidewall, or sidewalls, of valve chamber 27. In at least one such embodiment, seal 56a can prevent, or at least substantially prevent, fluid flowing through channel 2 and second valve chamber portion 29 from flowing into first valve chamber portion 28 and/or channel 1. Similarly, seal 56a can prevent, or at least substantially prevent, fluid flowing through channel 1 and first portion 28 from flowing into second portion 29 and/or channel 2. Similar to seal 56a, channel separator 50 can further include seal 56b which can be configured to engage the sidewalls of valve chamber 27 to prevent, or at least substantially prevent, fluid from escaping from valve chamber 27. In various embodiments, channel separator 50 can further include spring 59 and, in addition, protrusion 57 extending from valve element analogue 54, wherein spring 59 can be configured to apply a biasing force to protrusion 57 and bias valve element analogue 54 into valve chamber 27. In at least one embodiment, channel separator 50 can further include stop 55 extending therefrom wherein spring 59 can be configured to position valve element analogue 54 in valve chamber 27 such that stop 55 can abut, or is at least positioned adjacent to, surface 60 on control head section 23.

As a result of the above, channel separator 50 can sealingly separate channel 1 and channel 2 such that, when the channels are being tested for blockages or the presence of debris as outlined above, the fluid flowing through one of the channels may not flow into, or substantially flow into, the other channel. In the event, however, that seal 56a, for example, becomes cracked, chipped, and/or otherwise damaged, the fluid flowing through one of channels 1 and 2 during a flow rate test may flow into the other channel. For example, if seal 56a is somehow defective, the fluid flowing through channel 1 may flow past seal 56a into second portion 29. In such circumstances, the flow rate sensor 39 (FIG. 12) associated with channel 1 may detect a drop in the flow rate of the fluid flowing through channel 1. Such a drop in flow rate may also be consistent with an at least partially blocked channel and the decontamination apparatus may erroneously indicate to the operator that a blockage may exist within channel 1 when, in fact, the drop in flow rate is being caused by a faulty channel separator. Such circumstances may increase the time needed for the operator to detect the source of the problem.

In various circumstances, as outlined above, an endoscope, such as endoscope 21, for example, can include two or more channels which can converge into a common channel at a location positioned downstream from a valve chamber. For example, referring to FIG. 11, channels 1 and 2 of endoscope 21 can be in fluid communication with valve chamber portions 28 and 29, respectively, wherein channels 1 and 2 can converge at location 33 which is downstream from valve chamber 27. In such embodiments, in the event that fluid leaks between the channels, and/or the valve chamber portions of valve chamber 27, for example, during a fluid flow rate test, the flow of fluid through the endoscope may be divided across channels 1 and 2 but can be reconverged at downstream location 33, for example, before the flow rate of the fluid through the endoscope is evaluated. In such circumstances, a flow meter, or sensor, especially those placed downstream from distal end 34 of endoscope 21, such as sensor 44 (FIG. 12), for example, may not be able to discern that a channel separator is leaking as, ultimately, the net flow rate of the fluid exiting distal end 34 may be substantially unaffected.

In some circumstances, further to the above, a leak path between the channels and/or valve chambers of an endoscope may allow fluid flowing through a channel to be diverted around an obstruction in the channel. More particularly, in the event that the channel being tested is at least partially obstructed, at least a portion of the fluid may leak past a defective seal, or channel separator, into another channel which permits the fluid to, in effect, bypass the obstruction and, in various embodiments, reconverge with the fluid flowing through the channel being tested. In such circumstances, i.e., owing to a leaking test fixture, or channel separator, a decontamination apparatus may not be able to properly indicate to the operator that the flow rate through the channel being tested is less than expected. In order to reduce the occurrences of this condition, the channel separator can be examined prior to being used, and/or a preventive maintenance schedule can be employed, in order to reduce the possibility that a compromised seal and/or channel separator is used.

In various embodiments, further to the above, a test fixture, such as channel separator 50, for example, can be affixed to endoscope 21, for example, so as to hold valve analogues 54 and 96 within valve chambers 27 and 30, respectively. In at least one embodiment, referring to FIGS. 13 and 14, channel separator 50 can be configured to engage lock portions 23a and 23b of control head section 23 such that separator 50 can be locked to, and not readily removable from, endoscope 21. In certain embodiments, slide 52 of channel separator 50 can be configured to engage lock portions 23a and 23b when slide 52 is moved, or slid, between a first, or unlocked, position and a second, or locked, position. When slide 52 is in its unlocked position, slide 52 may not be engaged with, or only at least partially engaged with, lock portion 23a and/or lock portion 23b. When slide 52 is moved into its locked position, slide 52 can engage lock 23a and/or lock portion 23b such that channel separator 50 cannot be readily detached from endoscope 21 when an axial and/or transverse force is applied thereto, for example. In at least one such embodiment, slide 52 can include one or more lock portions, or flanges, 52a and 52b which can be configured to slide underneath endoscope lock portions 23a and/or 23b such that slide 52 is secured thereto. In various embodiments, lock portion 23a and/or 23b can comprise one or more lips, or projections, which can define one or more grooves, such as grooves 51a and 51b, for example, between the projections and the body of the control head section 23 as illustrated in FIG. 14. In certain embodiments, lock portion 23a and/or 23b can comprise annular, or at least substantially annular, projections surrounding valve chambers 27 and 30, respectively, wherein grooves 51a and 51b can comprise annular, or at least substantially annular, grooves extending around the perimeter of lock portions 23a and 23b, respectively. In any event, owing to the engagement of the endoscope lock portions 23a, 23b and lock flanges 52a, 52b, seals 56a, 56b, and 94 of channel separator 50 can be held in sealing engagement with their respective valve chambers. In certain circumstances, though, an operator may have to push downwardly on channel separator 50 so as to properly position valve analogues 54 and 96 within their respective valve chambers while, at the same time, push transversely on slide 52 in order to lock channel separator 50 in position. While such embodiments are suitable in many circumstances, some operators, however, may have difficulty in applying the necessary forces to operate channel separator 50. Discussed below are embodiments in which an operator can push downwardly on a channel separator to properly position one or more valve analogues in their valve chambers, but can release a slide, for example, to lock the channel separator in position. In any event, in order to remove channel separator 50 from endoscope 21, slide 52 can be moved from its second, or locked, position into its first, or unlocked, position such that flanges 52a, 52b are not engaged with, or only at least partially engaged with, lock portions 23a and 23b.

In various embodiments, referring now to FIGS. 1-9, a test fixture, such as channel separator 150, for example, can be affixed to endoscope 121, for example, so as to hold valve analogues, or shafts, 154 and 196 within valve chambers 127 and 130, respectively. Similar to the above, referring to FIGS. 3 and 4, first valve analogue 154 can be configured to sealingly separate valve chamber 127 into first portion 128 and second portion 129. Also similar to the above, valve analogue 154 can include a first seal 156a which can be configured to engage the sidewalls of valve chamber 127 and prevent, or at least inhibit, fluid flowing through first channel 101 from entering into second portion 129 and, correspondingly, fluid flowing through second channel 102 from entering into first portion 128. Further to the above, referring to FIG. 2, valve analogue 154 can further include a second seal 156b which can be configured to prevent fluid flowing through first channel 101 from escaping from control head section 123 via the open end of valve chamber 127. In various embodiments, referring again to FIG. 2, seal 156a and/or seal 156b can comprise o-ring seals, for example, wherein valve analogue 154 can include a first seal seat 154a configured to receive and retain first seal 156a therein and, in addition, second seal seat 154b configured to receive and retain second seal 156b therein. Similarly, second valve analogue 196 can comprise seal seat 196a which can be configured to receive and retain seal 194 therein, wherein seal 194 can be configured to sealingly engage the sidewalls of valve chamber 130.

Figure 1:
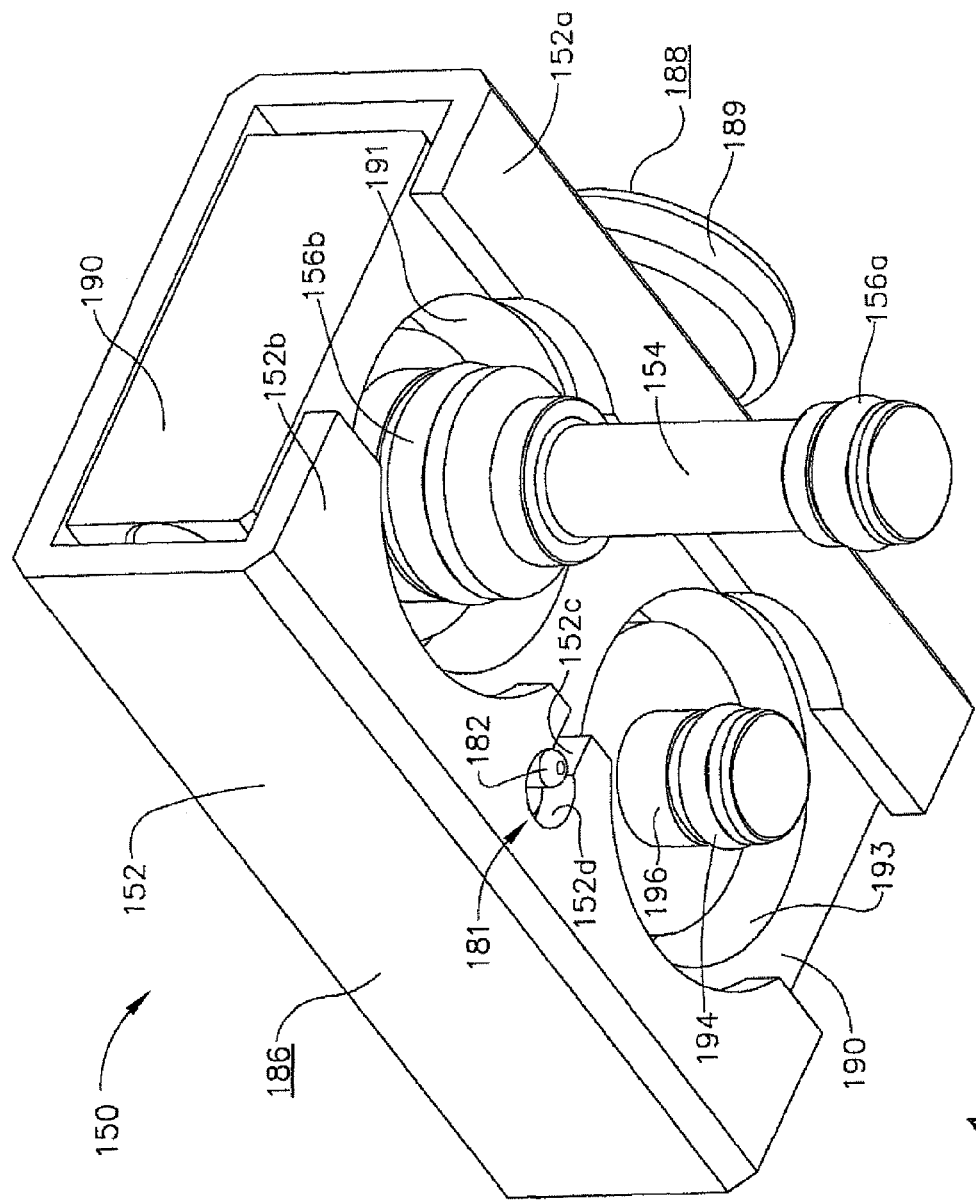
FIG. 1 is a perspective view of a test fixture, or channel separator, for use with an endoscope in accordance with at least one embodiment of the present invention.
Figure 2:
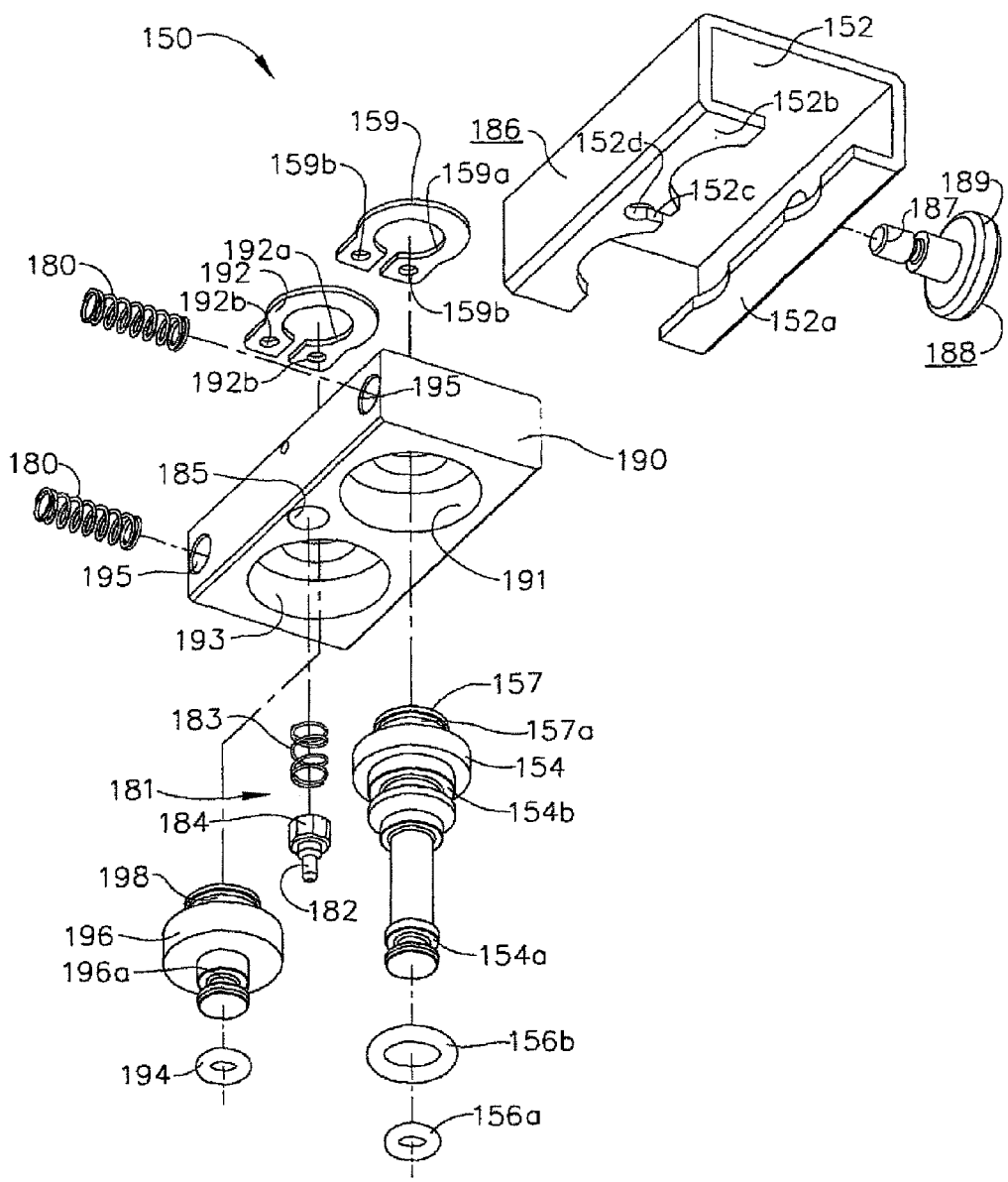
FIG. 2 is an exploded view of the channel separator of FIG. 1.
Figure 3:
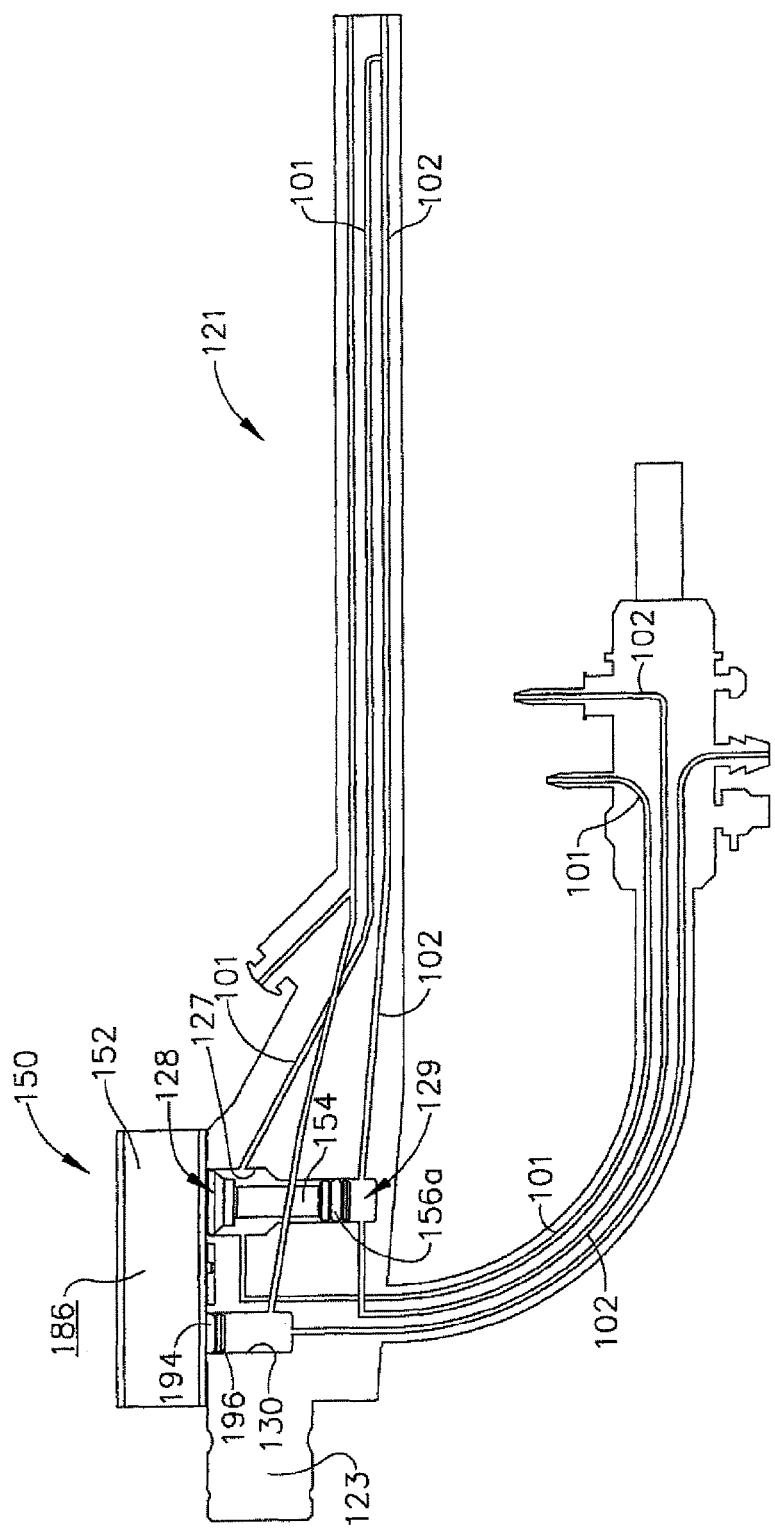
FIG. 3 is a schematic representation of an endoscope with the channel separator of FIG. 1 assembled thereto.
Figure 4:
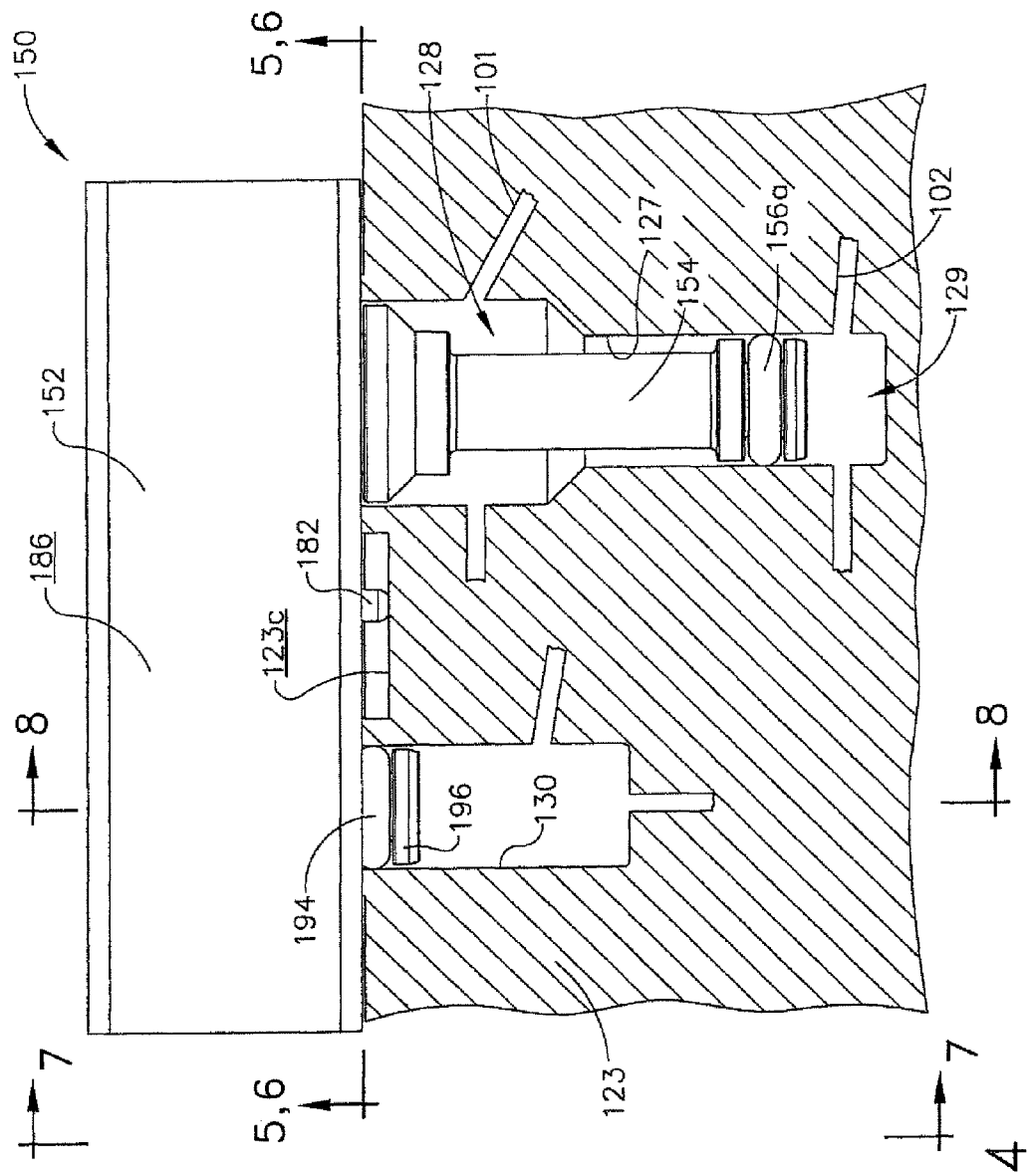
FIG. 4 is a detail view of the channel separator of FIG. 1 assembled to the endoscope of FIG. 3.

In various embodiments, referring to FIGS. 1 and 2, channel separator 150 can further include a block, or frame, 190 from which valve analogue 154 and/or valve analogue 196 can extend. In certain embodiments, although not illustrated, valve analogue 154 and/or valve analogue 196 can be integrally formed with, and/or threadably retained to, frame 190. In at least one embodiment, frame 190 can comprise a first aperture 191 configured to receive at least a portion of first valve analogue 154 therein and, in addition, a second aperture 193 configured to receive at least a portion of second valve analogue 196 therein. In certain embodiments, referring to FIGS. 2 and 8, channel separator 150 can further comprise one or more retainers configured to hold valve analogues 154 and 196 to frame 190. In at least one embodiment, channel separator 150 can include a first retaining member 159 mounted thereto, wherein retaining member 159 can comprise at least one aperture, such as aperture 159a, for example, which can be configured to receive at least a portion of the first valve analogue 154, such as retaining portion 157, therein. In at least one such embodiment, retaining portion 157 can comprise one or more grooves, such as groove 157a, for example, which can be configured to receive retaining member 159 therein such that retaining portion 157 and retaining member 159 can cooperate to retain valve analogue 154 to frame 190.

In various embodiments, referring again to FIG. 2, retaining member 159 can include at least one fastening aperture 159b configured to receive one or more fasteners (not illustrated) therein for attaching first retaining member 159 to frame 190. Similarly, channel separator 150 can further comprise a second retaining member 192 mounted to frame 190 via one or more fasteners (not illustrated) inserted through one or more fastener apertures 192b, wherein second retaining member 192 can be configured to retain second valve analogue 196 to frame 190. In at least one such embodiment, second retaining member 192 can comprise at least one aperture 192*a* which can be configured to receive retaining portion 198, for example, of second valve analogue 196 therein. In certain embodiments, first retaining member 159 and/or second retaining member 192, for example, can be comprised of one or more resilient, elastic, and/or suitably flexible materials which can be configured to permit retaining members 159 and/or 192 to act as a spring. In at least one embodiment, retaining members 159 and 192 can be comprised of spring steel and/or stainless steel. In some embodiments, referring to FIG. 2, retaining members 159 and/or 192 can be mounted to frame 190 at only one end thereof such that retaining members 159 and/or 192 can comprise cantilever springs.

In various embodiments, channel separator 150 can be assembled to endoscope 121 by aligning valve analogues 154 and 196 with valve chambers 127 and 130, respectively, positioning valve analogues 154 and 196 within valve chambers 127 and 130, and locking housing 152 to locking portions 123*a* and/or 123*b* of control head portion 123. In at least one embodiment, channel separator 150 can be configured such that housing 152 is movable between a first, or locked, position, and a second, or unlocked, position, wherein housing 152 can be held in its unlocked position (FIGS. 5 and 9) while valve analogues 154 and 196 are positioned within their respective valve chambers. In various embodiments, referring generally to FIG. 9, frame 190 can comprise a projection, or button, 189 extending therefrom which can include a first gripping surface 188 and, in addition, housing 152 can comprise a second gripping surface 186, wherein gripping surfaces 186 and 188 can be configured such that an operator can apply one or more forces to surfaces 186 and 188 in order to slide housing 152 relative to frame 190. In certain embodiments, second gripping surface 186 can be moved toward first gripping surface 188 in order to move housing 152 from its locked position, or configuration, into its unlocked position, or configuration. In at least one embodiment, referring to FIG. 2, projection 189 can include a threaded end 187 which can be engaged with frame 190 via a threaded aperture (not illustrated) therein.

In various embodiments, the operator can apply one or more compressive, or squeezing, forces to gripping surfaces 186 and 188, for example, to move housing 152 from its locked position into its unlocked position. In various embodiments, biasing members 180 can be positioned intermediate housing 152 and frame 190 such that, when housing 152 is moved relative to frame 190, biasing members 180 can be compressed therebetween. In at least one embodiment, referring to FIG. 9, biasing members 180 can comprise compression springs which can store energy therein as they are compressed. Referring to FIG. 9 once again, frame 190 can include one or more spring apertures 195 which can be sized and configured to receive at least a portion of biasing members 180 therein. Although not illustrated, embodiments are envisioned in which biasing members can comprise one or more tension springs positioned on the opposite side of frame 190, for example. In any event, once valve analogues 154 and 196 are positioned within their valve chambers, housing 152 can be released to allow biasing members 180 to move housing 152 into its locked position (FIGS. 6-8) as described in greater detail below. In certain embodiments, further to the above, biasing members 180 can be permitted to release at least a portion of the energy stored therein in order to return housing 152 to its locked configuration. In at least one embodiment, as a result, biasing members 180 can be configured to move second gripping surface 186 away from first gripping surface 188 and bias housing 152 into its locked position.

Figure 5:
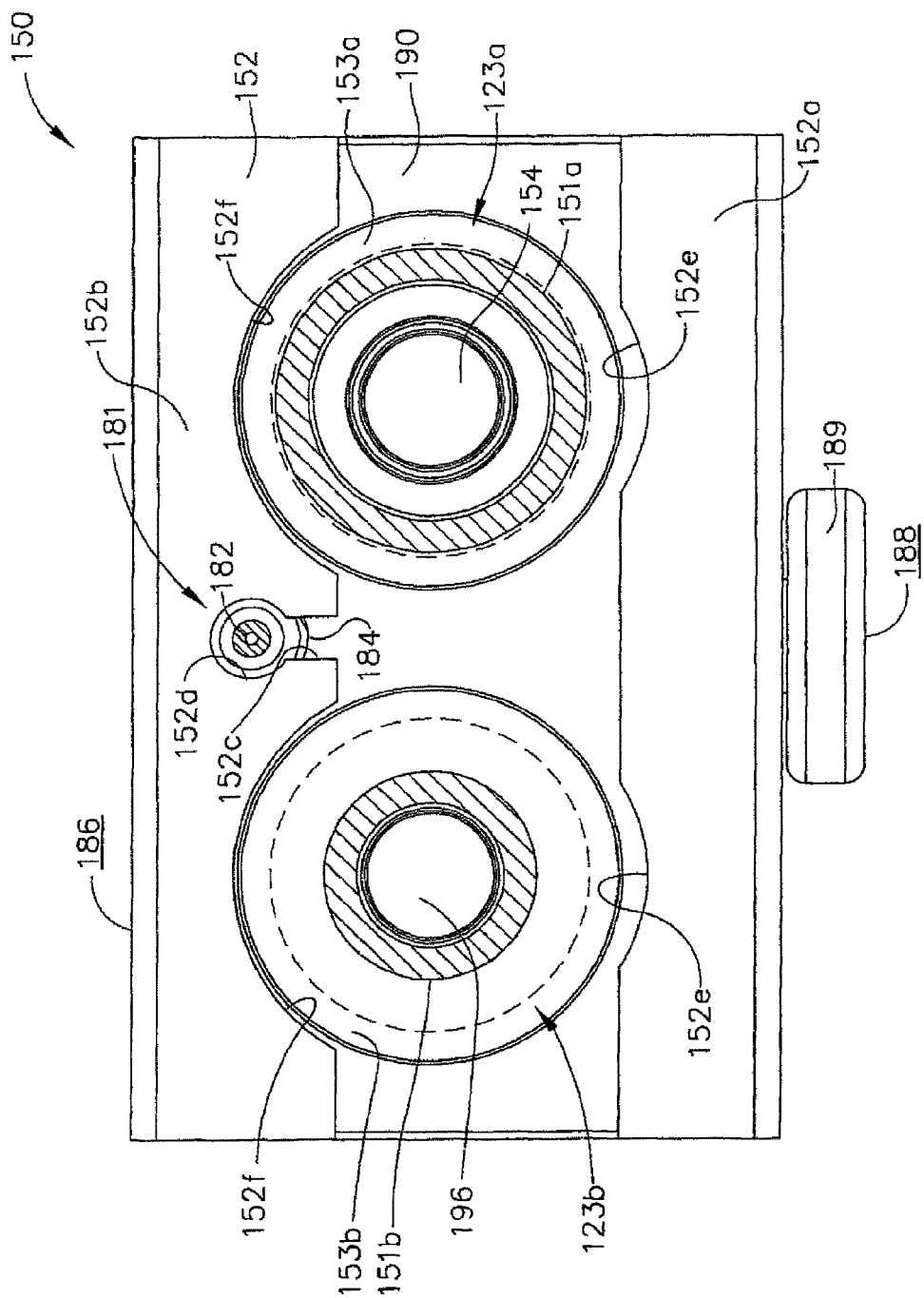
FIG. 5 is a bottom view of the channel separator of FIG. 1 illustrating the channel separator in an unlocked configuration and a partial cross-sectional view of the endoscope of FIG. 3 taken along line 5-5 in FIG. 4.
Figure 6:
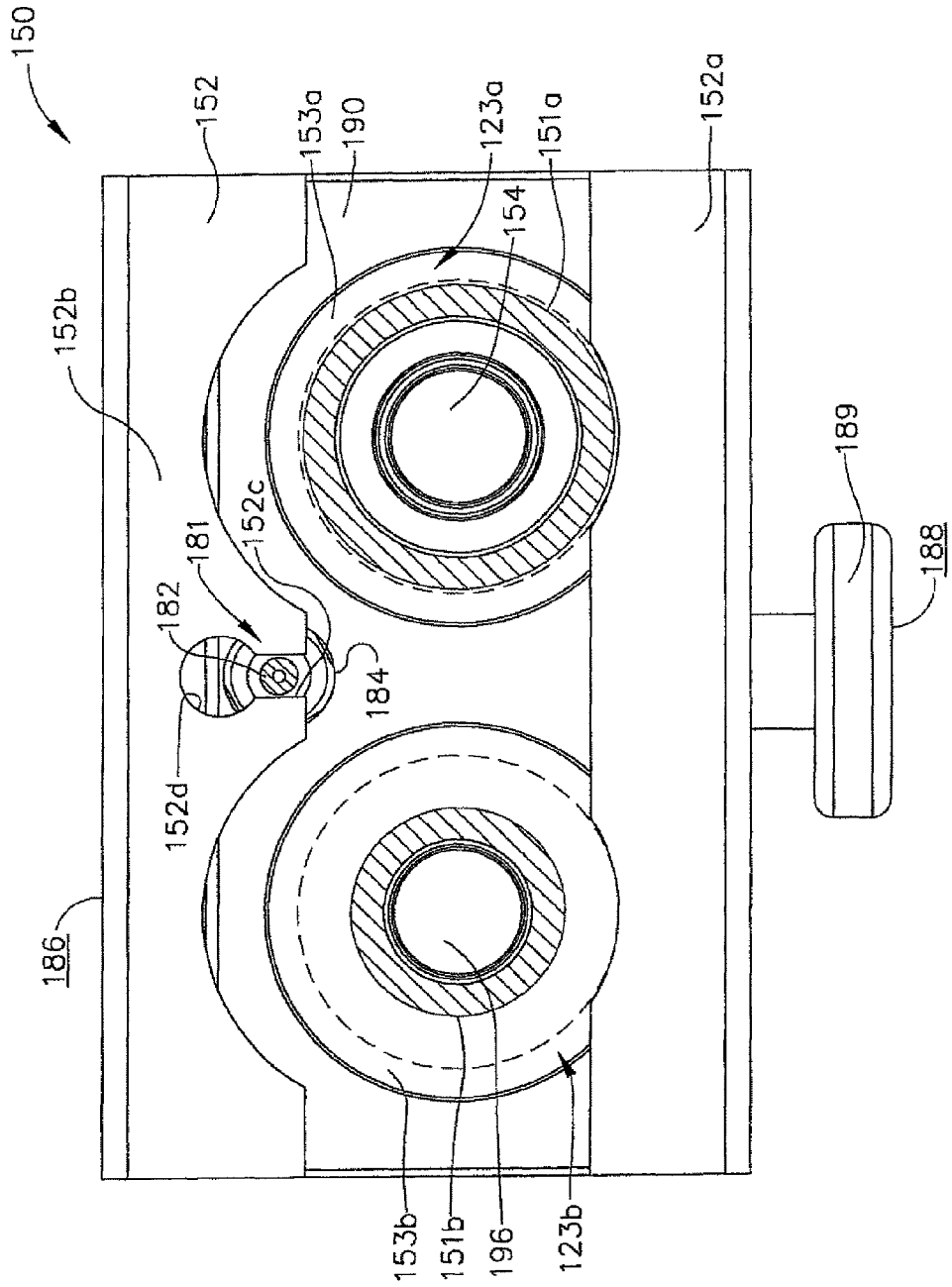
FIG. 6 is a bottom view of the channel separator of FIG. 1 illustrating the channel separator in a locked configuration and a partial cross-sectional view of the endoscope of FIG. 3 taken along line 6-6 in FIG. 4.

In various embodiments, referring to FIGS. 5 and 6, housing 152 can include at least one locking flange, such as locking flange 152*a*, for example, which can be configured such that it can be at least partially slid underneath endoscope locking portions 123*a* and 123*b* when housing 152 is moved from its unlocked position (FIG. 5) into its locked position (FIG. 6). In at least one embodiment, referring to FIG. 9, endoscope locking portion 123*a* can comprise at least one lip, or projection, 153*a* which can define at least one groove 151*a* positioned intermediate projection 153*a* and the body of control head section 123. Similarly, referring to FIG. 8, endoscope locking portion 123*b* can comprise at least one lip, or projection, 153*b* which can define at least one groove 151*b* positioned intermediate projection 153*b* and the body of control head section 123. When housing 152 is moved into its locked position, or configuration, at least a portion of lock flange 152*a* can be positioned underneath projections 153*a* and 153*b* and within grooves 151*a* and 151*b*. In various alternative embodiments, lock flange 152*a* may be configured to engage only one of locking portions 123*a* and 123*b*. In some embodiments, housing 152 can comprise more than one lock flange for engaging endoscope locking portions 123*a* and/or 123*b*, for example. In any event, owing to the cooperating geometries of endoscope locking portions 123*a*, 123*b* and lock flange 152*a*, channel separator 150 can be secured to endoscope 121, i.e., until housing 152 is moved into its unlocked position, or configuration, and lock flange 152*a* is removed from, or at least sufficiently removed from, grooves 151*a* and/or 151*b*.

Once lock flange 152*a* is sufficiently disengaged from endoscope locking portions 123*a* and/or 123*b*, for example, channel separator 150 can be detached from control head 123. In various embodiments, referring to FIG. 5 which illustrates housing 152 in an unlocked position, lock flange 152*a* can be moved such that lock flange 152*a* no longer overlaps endoscope locking projections 153*a* and 153*b*, as illustrated in FIG. 6. In such circumstances, locking portions 123*a* and 123*b* can be configured to moved relative to lock flange 152*a* and flange 152*b* through clearance cut-outs 152*e* and 152*f*, respectively. In at least one embodiment, an upward force can be applied to housing 152 and/or frame 190, for example, such that valve analogues 154 and 196 can be removed from valve chambers 127 and 130. In some circumstances, however, an operator may have to overcome a resistive force which can be generated by friction forces between seals 156*a*, 156*b*, and 194 and the sidewalls of the valve chambers. In various embodiments, channel separator 150, for example, can include a lifting mechanism which can be configured to push at least a portion of channel separator 150 away from control head section 123, for example, in order to facilitate the removal of channel separator 150. In at least one embodiment, referring to FIGS. 1 and 2, channel separator 150 can include lifting mechanism 181 which can be configured to engage control head section 123, for example, and move frame 190 upwardly when housing 152 is moved from its locked position to its unlocked position. In certain embodiments, lifting mechanism 181 can comprise at least one lifting member, such as lifting member 182, for example, and at least one biasing member, such as spring 183, for example, which can be configured to transmit a pushing force to control head section 123 and bias channel separator 150 upwardly.

Figure 7:
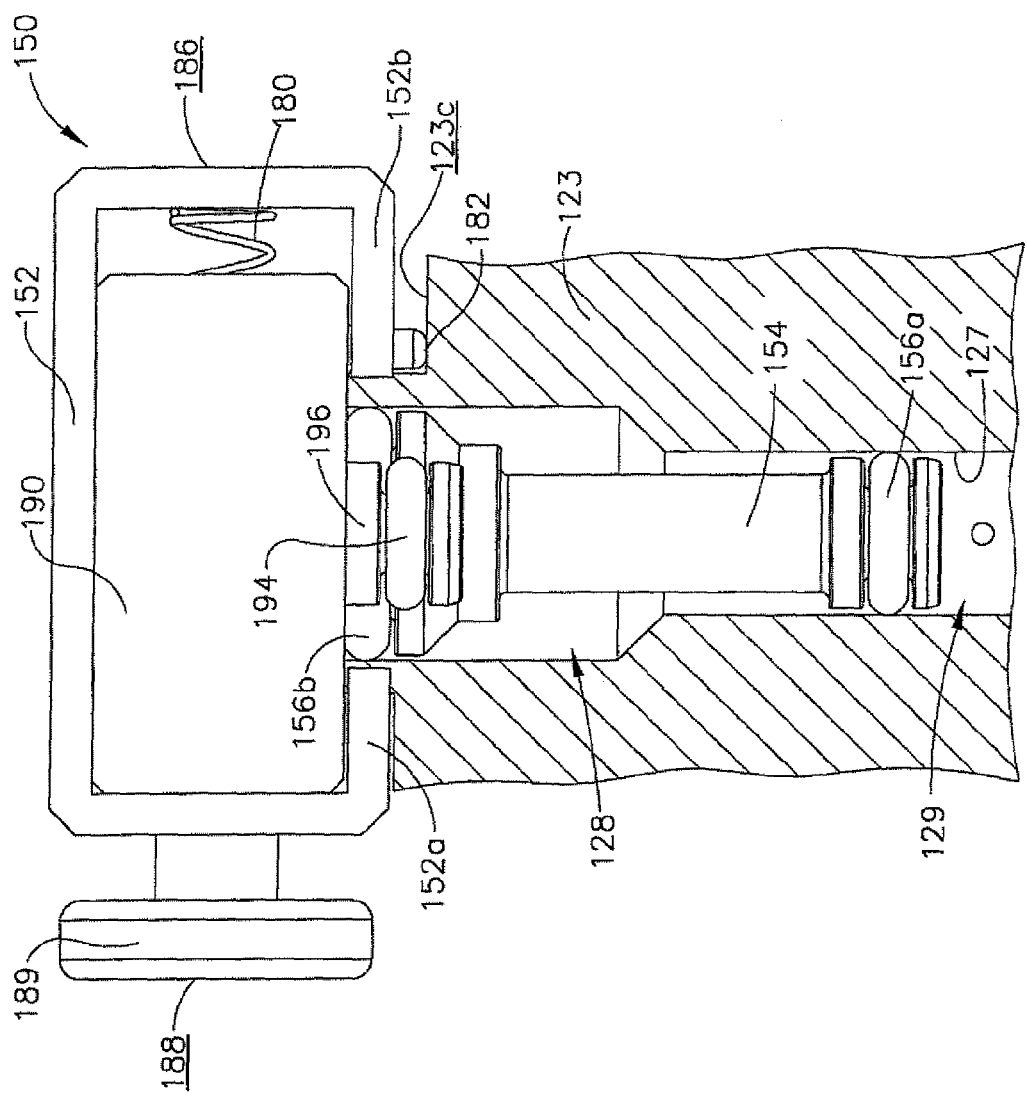
FIG. 7 is an end view of the channel separator of FIG. 1 illustrating the channel separator in a locked configuration and a partial cross-sectional view of the endoscope of FIG. 3 taken along line 7-7 in FIG. 4.
Figure 8:
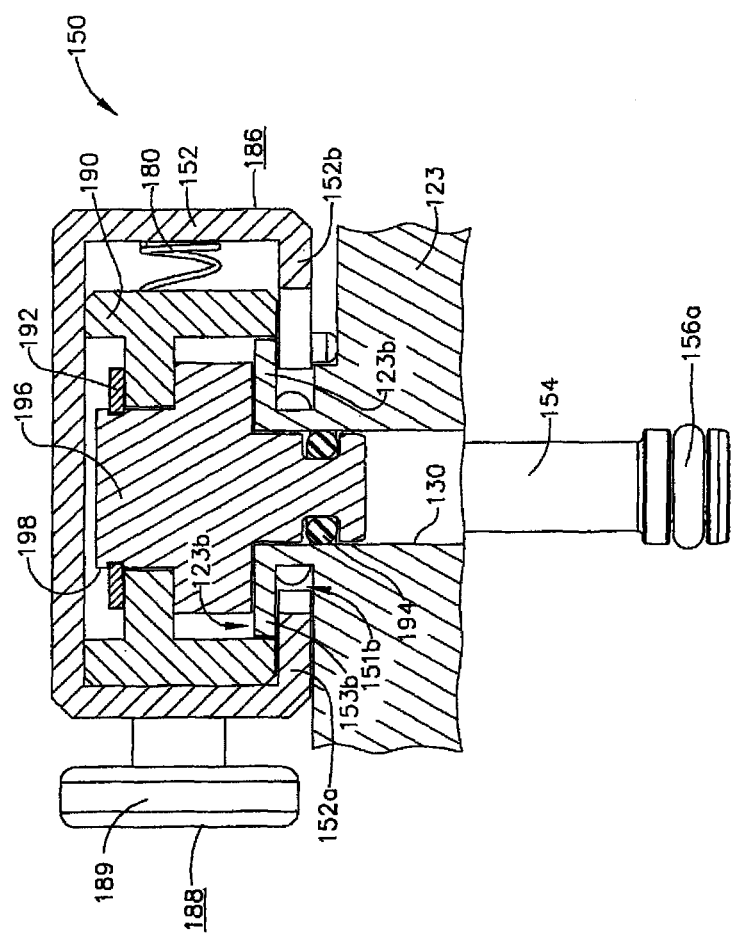
FIG. 8 is a cross-sectional view of the channel separator of FIG. 1 and the endoscope of FIG. 3 taken along line 8-8 in FIG. 4 illustrating the channel separator in a locked configuration.
Figure 9:
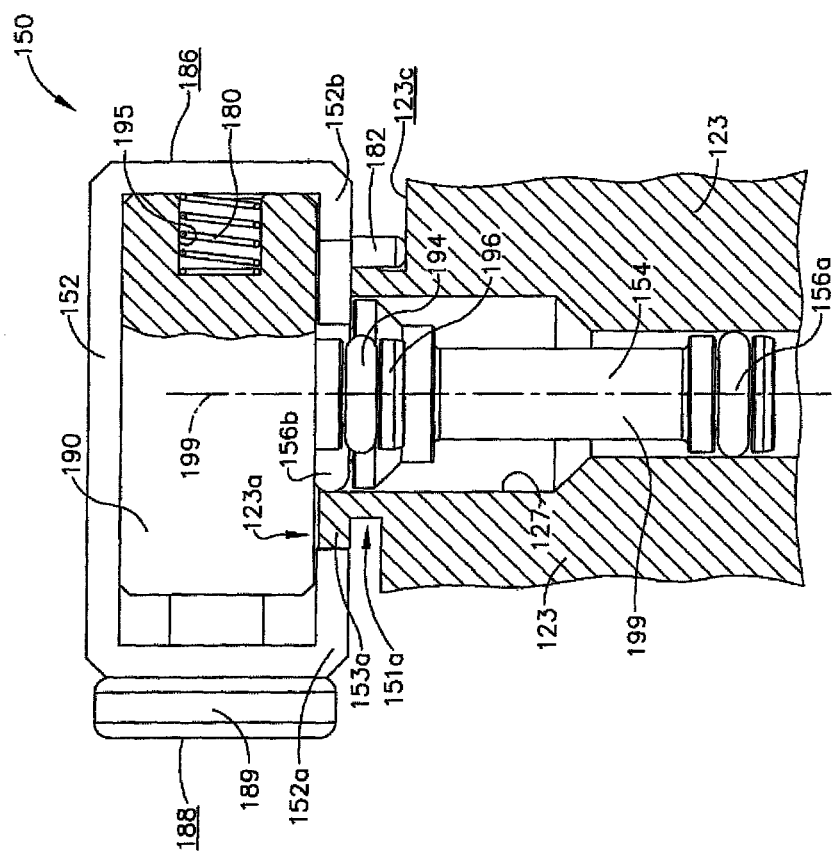
FIG. 9 is a partial cross-sectional view of the channel separator of FIG. 1 and the endoscope of FIG. 3 illustrating the channel separator in an unlocked configuration.

In various embodiments, referring to FIG. 6 which illustrates housing 152 in its locked position, lifting member 182 can be maintained in a first position by flange 152*b* of housing 152 such that lifting member 182 may not engage, or at least substantially engage, pushing surface 123c on control head section 123 as illustrated in FIG. 7. In at least one embodiment, referring again to FIG. 6, flange 152b can further include slot 152c therein which can permit lifting member 182 to at least partially extend therethrough, yet releasably retain lifting member 182 in its first position. When housing 152 is moved into its unlocked position, as illustrated in FIG. 5, aperture 152d of slot 152c can be aligned with lifting member 182 such that lifting member 182 can be moved into its extended position (FIG. 9) by spring 183. In at least one such embodiment, aperture 152d can be sized and configured so as to allow a greater portion of lifting member 182 to extend therethrough, yet prevent, or at least inhibit, enlarged portion 184 of lifting member 182 from entirely passing therethrough. Such embodiments can prevent, or at least inhibit, lifting member 182 from becoming completely detached from channel separator 150. In certain embodiments, referring to FIG. 2 once again, frame 190 can include aperture 185 which can be configured to receive at least a portion of spring 183 and/or lifting member 182, wherein spring 183 can be positioned intermediate frame 190 and lifting member 182.

In various embodiments, further to the above, a lifting mechanism can be configured to push the channel separator upwardly, i.e., along an axis, or substantially along an axis, defined by valve chamber 127 and/or valve chamber 130. In at least one such embodiment, although not illustrated, the lifting mechanism can be positioned along, or at least substantially along, the midline, or midplane, of the channel separator such that little, if any, torque or moment is generated when the lifting mechanism lifts the channel separator upwardly. In certain embodiments, a lifting mechanism can be configured to rock, tilt, or rotate the channel separator when the lifting mechanism engages the endoscope. In at least one embodiment, referring to FIG. 9, lifting mechanism 181 can be attached to channel separator 150 such that it is positioned on one side of the midline, or midplane, of the channel separator. In various embodiments, lifting mechanism 181 can be configured such that lifting member 182 contacts control head section 123 along a line which is not collinear, or at least substantially collinear, with midline 199 of frame 190. Owing to the offset of lifting member 182, frame 190 may rock, tilt, or rotate relative to endoscope locking portions 123a and/or 123b, for example, such that the side of housing 152 having lifting mechanism 181 is positioned higher than the other side of housing 152, for example.

In various embodiments, further to the above, housing 152 can be moved into its unlocked position by moving housing 152 relative to frame 190 in a direction which is transverse to axes defined by valve analogues, or shafts, 154 and/or 156. In certain embodiments, housing 152 can be moved in a direction which is perpendicular to, or at least substantially perpendicular to, such axes. In at least one embodiment, valve analogues 154 and 196 can be inserted into valve chambers 127 and 130 along a direction which is substantially parallel to, or substantially collinear with, the axes defined by valve analogues 154 and/or 156. Once positioned, housing 152 can be released such that it moves into its locked position in a direction which is transverse to such axes. In certain embodiments, housing 152 can be engaged with and/or disengaged from locking portions 123a and/or 123b in a direction which is perpendicular, or at least substantially perpendicular, to these axes. In various embodiments, housing 152 can engage and/or disengage locking portions 123a and/or 123b from their sides either sequentially or simultaneously. In at least one embodiment, locking portions 123a and 123b can define a line therebetween in which housing 152 can engage and/or disengage locking portions 123a and/or 123b in a direction which is transverse, perpendicular, and/or skew with respect to such a line. In certain embodiments, the direction in which housing 152 engages and/or disengages locking portions 123a and/or 123b is not parallel to or collinear with this line.

As outlined above, in various embodiments, a channel separator, or test fixture, can include two valve analogues for sealing two valve chambers. In certain embodiments, a channel separator, or test fixture, can include one valve analogue or, alternatively, more than two valve analogues which can be respectively inserted into more than two valve chambers. In at least one such embodiment, a channel separator can include three valve analogues which can be inserted into three valve chambers. In various embodiments, further to the above, the channel separator can include a housing which engages locking portions associated with each valve chamber. In certain other embodiments, the channel separator can include a housing which engages less than all of the locking portions associated with the valve chambers. In at least one embodiment, the valve chambers, and locking portions associated therewith, can be positioned along a line, or arranged in any other suitable pattern, and the housing can be configured to engage the locking portions associated with the valve chambers on the ends of the line or pattern. Stated another way, the movable housing can be locked to an endoscope by engaging two or more locking portions but not engaging one or more locking portions therebetween. In certain other embodiments, the housing may not engage the locking portions associated with valve chambers on the ends of the line or pattern.

In various embodiments, housing 152, frame 190, and/or valve analogues 154 and 196 of channel separator 150, for example, can be comprised of any suitable material, such as stainless steel 316, for example, wherein seals 156a, 156b, and/or 194, for example, can be comprised of silicone, for example. In certain circumstances, channel separator 150 may need to be sterilized and, in certain embodiments, housing 152, frame 190, and/or the valve analogues 154, 196 can be disassembled such that they can be cleaned, reassembled, and reused. In certain other embodiments, channel separator 150, for example, can comprise one or more disposable components which can be discarded after one or more uses. In at least one such embodiment, valve analogues 154 and/or 196 can be comprised of plastic and can be easily assembled to and disassembled from frame 190, for example. In various embodiments, as a result, one or more of the valve analogues can be disposable. In certain embodiments, seals 156a, 156b, and/or 194 can be assembled to valve analogues 154 and/or 196, respectively, while, in other embodiments, seals can be integrally formed with the valve analogues. In at least one such embodiment, seals 156a and/or 156b can be integrally formed with valve analogue 154, for example, such that, after seals 156a and/or 156b have become worn or cracked, the entire valve analogue assembly can be disposed of. In certain embodiments, the integral seals and valve analogue can be comprised of silicone.

Although the embodiments disclosed herein have been described in connection with an endoscope, other embodiments are envisioned in connection with any suitable medical device. While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A test fixture, comprising:
a frame having a first gripping portion;
a valve member analogue extending from said frame, wherein said valve member analogue includes a seal configured to seal at least a portion of a valve chamber of an endoscope when a removable valve of the endoscope is removed from the valve chamber, and another seal configured to separate a first channel of the valve chamber of the endoscope from a second channel of the valve chamber of the endoscope when the removable valve of the endoscope is removed from the valve chamber;
another valve member analogue extending from said frame, wherein said valve member analogue and said another valve member analogue define a longitudinal axis extending substantially therebetween;
retainers attached to said frame and holding said valve member analogues to said frame, wherein said retainers prevent said valve member analogues from moving relative to said frame;
a housing movable relative to said frame, wherein said frame is located within said housing and said housing is movable substantially perpendicular to said longitudinal axis between a locked position and an unlocked position, wherein said housing comprises a second gripping portion, wherein said second gripping portion is configured to be moved toward said first gripping portion to position said housing in said unlocked position, wherein said second gripping portion is configured to be moved away from said first gripping portion to position said housing in said locked position, and wherein said housing comprises a second locking feature configured to engage a first locking feature of the endoscope when said second gripping portion is moved away from said first gripping portion.

2. The test fixture of claim 1, further comprising a spring positioned intermediate said housing and said frame, wherein said spring is configured to bias said housing substantially perpendicular to said longitudinal axis into said locked position.

3. The test fixture of claim 1, further comprising:
a lifting member movable relative to said frame, wherein said lifting member is movable between a first position and an extended position, and wherein said lifting member is configured to engage the endoscope when said lifting member is in said extended position; and
a spring positioned intermediate said lifting member and said frame, wherein said spring is configured to apply a biasing force to said lifting member to move said lifting member into said extended position.

4. The test fixture of claim 3, wherein said frame includes a midline, wherein said lifting member is positioned on one side of said midline, and wherein said lifting member and said spring are configured to tilt said frame relative to the endoscope when said lifting member is in said extended position.

5. The test fixture of claim 3, wherein said housing is configured to retain said lifting member in said first position when said housing is in said locked position, and wherein said housing includes a slot configured to permit said spring to move said lifting member into said extended position when said housing is moved into said unlocked position.

6. The test fixture of claim 1, wherein said valve member analogue comprises a disposable valve member analogue removably connected to said frame.

7. The test fixture of claim 1, wherein the endoscope includes a plurality of first locking features and a plurality of valve chambers, wherein said valve member analogue and said another valve member analogue are configured to correspond with a corresponding said valve chamber, and wherein said housing further comprises a plurality of second locking features configured to engage said plurality of first locking features.

8. A test fixture, comprising:
a frame;
a valve member analogue extending from said frame, wherein said valve member analogue includes a first seal and a second seal, wherein the first and second seals are configured to seal at least a portion of a valve chamber of an endoscope when a removable valve of the endoscope is removed from the valve chamber;
another valve member analogue extending from said frame, wherein said valve member analogue and said another valve member analogue define a longitudinal axis extending substantially therebetween;
retainers attached to said frame and holding said valve member analogues to said frame, wherein said retainers prevent said valve member analogues from moving relative to said frame;
a housing movable relative to said frame, wherein said frame is located within said housing and said housing is movable substantially perpendicular to said longitudinal axis toward said frame to position said housing in an unlocked position; and
a biasing member configured to bias said housing to said frame substantially perpendicular to said longitudinal axis to position said housing in a locked position in which said housing is locked to a locking feature of the endoscope.

9. The test fixture of claim 8, further comprising:
a lifting member movable relative to said frame, wherein said lifting member is movable between a first position and an extended position, and wherein said lifting member is configured to engage the endoscope when said lifting member is in said extended position; and
a spring positioned intermediate said lifting member and said frame, wherein said spring is configured to apply a biasing force to said lifting member to move said lifting member into said extended position.

10. The test fixture of claim 9, wherein said frame includes a midline, wherein said lifting member is positioned on one side of said midline, and wherein said lifting member and said spring are configured to tilt said frame relative to the endoscope when said lifting member is in said extended position.

11. The test fixture of claim 9, wherein said housing is configured to retain said lifting member in said first position when said housing is in said locked position, and wherein said housing includes a slot configured to permit said spring to move said lifting member into said extended position when said housing is moved into said unlocked position.

12. The test fixture of claim 8, wherein said valve member analogue comprises a disposable valve member analogue removably connected to said frame.

13. The test fixture of claim 8, wherein the endoscope includes a plurality of locking features and a plurality of valve chambers, wherein said valve member analogue and said another valve member analogue are configured to correspond with a corresponding said valve chamber, and wherein said housing is configured to be locked to said plurality of locking features.

14. A test fixture, comprising:
  a frame;
  a valve member analogue extending from said frame, wherein said valve member analogue includes a seal configured to seal at least a portion of a valve chamber of an endoscope when a removable valve is removed from the valve chamber, and wherein said seal is configured to separate a first channel of the valve chamber of the endoscope from a second channel of the valve chamber of the endoscope;
  another valve member analogue extending from said frame, wherein said valve member analogue and said another valve member analogue define a longitudinal axis extending substantially therebetween;
  retainers attached to said frame and holding said valve member analogues to said frame, wherein said retainers prevent said valve member analogues from moving relative to said frame; and
  a housing configured to lock the test fixture to the endoscope, wherein said frame is located within said housing.

15. The test fixture of claim 14, further comprising a spring positioned intermediate said housing and said frame, wherein said spring is configured to bias said housing into a locked configuration.

16. The test fixture of claim 14, further comprising:
  a lifting member movable relative to said frame, wherein said lifting member is movable between a first position and an extended position, and wherein said lifting member is configured to engage the endoscope when said lifting member is in said extended position; and
  a spring positioned intermediate said lifting member and said frame, wherein said spring is configured to apply a biasing force to said lifting member to move said lifting member into said extended position.

17. The test fixture of claim 16, wherein said frame includes a midline, wherein said lifting member is positioned on one side of said midline, and wherein said lifting member and said spring are configured to tilt said frame relative to the endoscope when said lifting member is in said extended position.

18. The test fixture of claim 16, wherein said housing is configured to releasably retain said lifting member in said first position until said housing is configured in an unlocked configuration.

19. The test fixture of claim 14, wherein said valve member analogue comprises a disposable valve member analogue removably connected to said frame.

20. The test fixture of claim 14, wherein the endoscope includes a plurality of locking features and a plurality of valve chambers, wherein said valve member analogue and said another valve member analogue are configured to correspond with a corresponding said valve chamber, and wherein said housing is configured to lock to said plurality of locking features.

* * * * *